US009205266B2

(12) United States Patent
Kothandaraman et al.

(10) Patent No.: US 9,205,266 B2
(45) Date of Patent: *Dec. 8, 2015

(54) SEAMLESS INTEGRATION OF DIFFERENT PROGRAMMING MODES FOR A NEUROSTIMULATOR PROGRAMMING SYSTEM

(71) Applicant: BOSTON SCIENTIFIC NEUROMODULATION CORPORATION, Valencia, CA (US)

(72) Inventors: Sridhar Kothandaraman, Valencia, CA (US); Dongchul Lee, Agua Dulce, CA (US); Mun Pook Lui, Northridge, CA (US)

(73) Assignee: Boston Scientific Neuromodulation Corporation, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,949

(22) Filed: Nov. 18, 2014

(65) Prior Publication Data

US 2015/0073504 A1    Mar. 12, 2015

Related U.S. Application Data

(63) Continuation of application No. 14/155,256, filed on Jan. 14, 2014, now Pat. No. 8,958,884, which is a continuation of application No. 13/715,751, filed on Dec. 14, 2012, now Pat. No. 8,660,653.

(60) Provisional application No. 61/576,924, filed on Dec. 16, 2011.

(51) Int. Cl.
*A61N 1/00* (2006.01)
*A61N 1/36* (2006.01)
*A61N 1/372* (2006.01)

(52) U.S. Cl.
CPC .......... *A61N 1/36185* (2013.01); *A61N 1/3605* (2013.01); *A61N 1/36071* (2013.01); *A61N 1/37247* (2013.01); *A61N 1/37264* (2013.01)

(58) Field of Classification Search
CPC ........... A61N 1/36185; A61N 1/37247; A61N 1/37264; A61N 1/36071; A61N 1/3605
See application file for complete search history.

(56) References Cited

U.S. PATENT DOCUMENTS 6,516,227 B1   2/2003   Meadows et al.
6,895,280 B2   5/2005   Meadows et al.
(Continued)

FOREIGN PATENT DOCUMENTS

JP   2010527675 A   8/2010
JP   2013524947 A   6/2013
(Continued)

OTHER PUBLICATIONS

U.S. Appl. No. 61/452,965, Neurostimulation System for Defining a Generalized Ideal Multipole Configuration, Inventor: Dongchul Lee, et al., filed Mar. 15, 2011.
(Continued)

*Primary Examiner* — Robert N Wieland
(74) *Attorney, Agent, or Firm* — Schwegman Lundberg & Woessner, P.A.

(57) ABSTRACT

A system and method for programming a neurostimulation device coupled to a plurality of electrodes implanted adjacent tissue of a patient are provided. A first electrode configuration corresponding to a first mode of programming the neurostimulation device is defined. A second programming mode of programming the neurostimulation device different from the first programming mode is selected. A second electrode configuration is defined based on the first electrode configuration in response to the selection of the second programming mode. The neurostimulation device is programmed using the second programming mode.

20 Claims, 16 Drawing Sheets

(56) References Cited

U.S. PATENT DOCUMENTS

| | | | |
|---|---|---|---|
| 6,993,384 B2 | 1/2006 | Bradley et al. | |
| 7,239,926 B2 * | 7/2007 | Goetz | 607/148 |
| 8,660,653 B2 | 2/2014 | Kothandaraman et al. | |
| 8,958,884 B2 | 2/2015 | Kothandaraman et al. | |
| 2007/0245318 A1 | 10/2007 | Goetz et al. | |
| 2008/0183256 A1 | 7/2008 | Keacher | |
| 2010/0010566 A1 | 1/2010 | Thacker et al. | |
| 2010/0121409 A1 | 5/2010 | Kothandaraman et al. | |
| 2011/0040547 A1 | 2/2011 | Gerber et al. | |
| 2011/0078900 A1 | 4/2011 | Pianca et al. | |
| 2011/0093047 A1 | 4/2011 | Davis et al. | |
| 2011/0106215 A1 | 5/2011 | Moffitt | |
| 2014/0172046 A1 | 6/2014 | Kothandaraman et al. | |

FOREIGN PATENT DOCUMENTS

| | | | |
|---|---|---|---|
| JP | 2015500711 A | 1/2015 | |
| WO | WO-2010124144 A1 | 10/2010 | |
| WO | WO-2011133564 A1 | 10/2011 | |
| WO | WO-2013090819 A1 | 6/2013 | |

OTHER PUBLICATIONS

PCT International Search Report for PCT/US12/069915, Applicant: Boston Neuromodulation Corporation, Form PCT/ISA/210 and 220, dated Feb. 27, 2013 (8pages).

PCT Written Opinion of the International Search Authority for PCT/US12/069915, Applicant: Boston Neuromodulation Corporation, Form PCT/ISA/237, dated Feb. 27, 2013 (8pages).

"U.S. Appl. No. 13/715,751, Notice of Allowance mailed Oct. 15, 2013", 10 pgs.

"U.S. Appl. No. 14/155,256, 312 Amendment filed Nov. 4, 2014", 5 pgs.

"U.S. Appl. No. 14/155,256, Notice of Allowance mailed Sep. 25, 2014", 9 pgs.

"U.S. Appl. No. 14/155,256, PTO Response to Rule 312 Communication mailed Nov. 20, 2014", 2 pgs.

"Australian Application Serial No. 2012352009, First Examiner Report mailed Sep. 4, 2014", 3 pgs.

"European Application Serial No. 12809520.5, Office Action mailed Jul. 29, 2014", 2 pgs.

"International Application Serial No. PCT/US2012/069915, International Preliminary Report on Patentability mailed Jul. 18, 2014", 10 pgs.

* cited by examiner

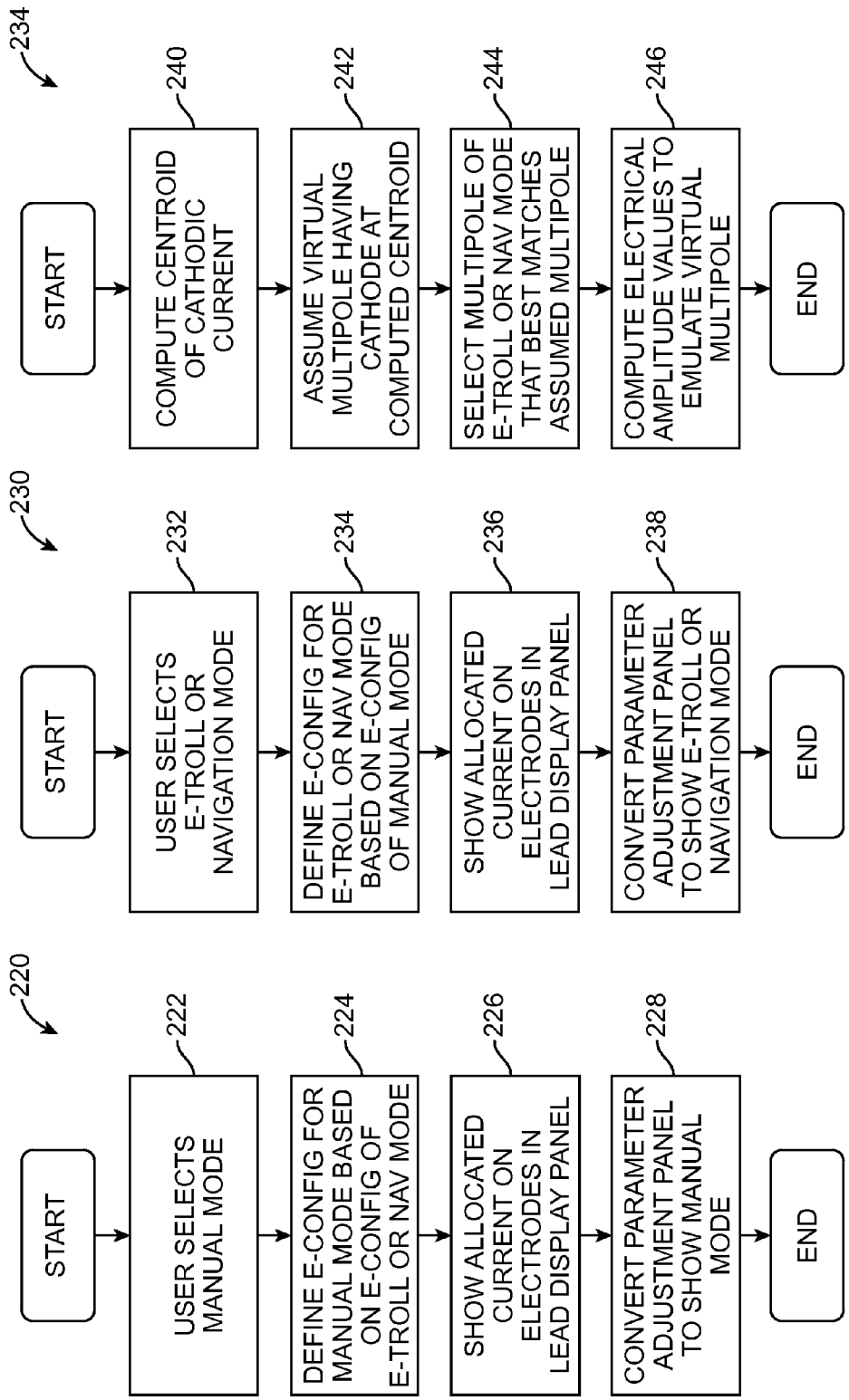

SEAMLESS INTEGRATION OF DIFFERENT PROGRAMMING MODES FOR A NEUROSTIMULATOR PROGRAMMING SYSTEM

RELATED APPLICATION DATA

The present application is a continuation of U.S. patent application Ser. No. 14/155,256, now issued as U.S. Pat. No. 8,958,884, which is a continuation of U.S. patent application Ser. No. 13/715,751, filed Dec. 14, 2012, now issued as U.S. Pat. No. 8,660,653, which claims the benefit under 35 U.S.C. §119 to U.S. Provisional Patent Application Ser. No. 61/576,924, filed Dec. 16, 2011. The foregoing applications are expressly incorporated herein by reference.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

To determine the stimulation parameters to be programmed, the Bionic Navigator® may be operated by a clinician in one of three modes: (a) a manual programming mode to manually select the cathodic current and anodic current flowing through the electrodes; (b) an electronic trolling ("e-troll") mode to quickly sweep the electrode array using a limited number of electrode configurations to gradually move a cathode in bipolar stimulation; and (c) a Navigation programming mode to fine tune and optimize stimulation coverage for patient comfort using a wide number of electrode configurations. These three modes allow the clinician to determine the most efficient stimulation parameter sets for a given patient.

In the manual programming mode, the clinician directly selects individual electrodes and the current magnitude and polarity to be applied to each selected electrode. In the navigation and e-troll programming modes, the Bionic Navigator® semi-automatically transitions between different electrode configurations to electrically "steer" the current along the implanted leads in real-time (e.g., using a joystick or joystick-like controls) in a systematic manner, thereby allowing the clinician to determine the most efficacious stimulation parameter sets that can then be stored and eventually combined into stimulation programs. In the context of SCS, current steering is typically either performed in a rostro-caudal direction (i.e., along the axis of the spinal cord) or a medial-lateral direction (i.e., perpendicular to the axis of the spinal cord).

The navigation and e-troll programming modes differ in part in the way in which the clinician changes electrode configurations from one configuration to another. E-troll programming mode utilizes a technique known as "panning", which shifts a pre-defined electrode configuration down the sequence of electrodes without changing the basic form of the electrode configuration. Navigation programming mode utilizes a technique known as "weaving," which moves the anode or anodes around the cathode, while slowly progressing the cathode down the sequence of electrodes. The e-troll and Navigation programming modes may have different clinical uses (e.g., finding the "sweet spot" in the case of panning, or shaping the electrical field around the cathode in the case of weaving).

In one novel current steering method, described in U.S. patent application Ser. No. 12/938,282, entitled "System and Method for Mapping Arbitrary Electric Fields to Pre-existing Lead Electrodes," which is expressly incorporated herein by reference, a stimulation target in the form of a virtual pole (e.g., a virtual bipole or tripole) is defined and the stimulation parameters, including the fractionalized current values on each of the electrodes, are computationally determined in a manner that emulates these virtual poles. It can be appreciated that current steering can be implemented by moving the virtual poles about the leads, such that the appropriate fractionalized current values for the electrodes are computed for each of the various positions of the virtual pole. As a result, the current steering can be implemented using an arbitrary number and arrangement of electrodes, thereby solving the aforedescribed problems.

The virtual bipole or tripole can be determined using a simplified virtual tripole consisting of a cathode, and an upper (or rostral) anode and lower (or caudal) electrode located on a longitudinal axis from the cathode. The virtual tripole may be defined using three values consisting of (1) location of the cathode relative to the electrodes; (2) a focus, which is the distance between the cathode and the anode(s); and (3) a percentage of current on the upper cathode. This technique is described in U.S. Provisional Patent Application Ser. No. 61/452,965, entitled "Neurostimulation System for Defining a Generalized Virtual Multipole," which is expressly incorporated herein by reference.

When used by itself, operating the Bionic Navigator® in just the manual programming mode may be a tedious and time consuming task. In practice, it is very useful to use either the e-troll programming mode or the Navigation programming mode to quickly determine the general electrode configuration of interest and then fine tune using the manual programming mode to add/remove anodes/cathodes to provide the optimal stimulation. The reverse is also true in that, clinicians may have the knowledge to manually configure the electrodes to get the therapeutic effect very close to the optimal electrode configuration, and then the e-troll programming mode or Navigation programming mode can be used to optimize the therapy around the manually selected electrode configuration.

Both Navigation programming mode and e-troll programming mode allow only a subset of configurations possible in manual programming mode. Because the configurations possible in each mode are not always available in the other non-manual programming modes, switching between modes has been cumbersome. Typically, switching between modes lost all information about the carefully adjusted configuration in the previous mode, and required starting from a default configuration in the new mode, then using the new mode to adjust the default configuration.

SUMMARY OF THE INVENTION

In accordance with a first aspect of the present inventions, a system for programming a medical device coupled to a plurality of electrodes is provided. The system comprises a user interface including a programming selection control element configured for allowing a user to select one of two different programming modes for the medical device. The system further comprises processing circuitry configured for defining a first electrode configuration corresponding to the first programming mode, selecting the second programming mode in response to actuation of the programming selection control element, and defining a second electrode configuration in response to the selection of the second programming mode. The second electrode configuration corresponds to the second programming mode. In one embodiment, the first electrode configuration is not a valid electrode configuration for the second programming mode. In another embodiment, the second electrode configuration approximates the first electrode configuration. Each of the first and second electrode configurations may be, e.g., a fractionalized electrode configuration.

The system further comprises control circuitry configured for generating a stimulation parameter set corresponding to the second electrode configuration, and instructing the medical device to convey electrical energy to the plurality of electrodes in accordance with the stimulation parameter set.

In another embodiment, the first programming mode is one of a manual programming mode and a semi-automated programming mode, and the second programming mode is the other of the manual programming mode and the semi-automated programming mode. In this case, the processing circuitry may be configured for defining a virtual multipole relative to the plurality of electrodes when programming the medical device in the semi-automated mode, and computing amplitude values for the plurality of electrodes that emulate the virtual multipole. The stimulation parameter set includes the computed amplitude values. The semi-automated programming mode may, e.g., be configured for panning the virtual multipole across the plurality of electrodes or displacing at least one anode of the virtual multipole relative to the a cathode of the virtual multipole as the cathode is gradually displaced across the plurality of electrodes.

In still another embodiment, the first programming mode is the manual programming mode, and the second programming mode is the semi-automated programming mode. In this case, the processing circuitry may be configured for defining the second electrode configuration by computing a centroid of cathodic current of the first electrode configuration, defining a virtual multipole having a virtual cathode located at the centroid of the cathodic current, and computing current amplitude values for the plurality of electrodes that emulates the virtual multipole, thereby defining the second electrode configuration.

In yet another embodiment, the first programming mode is the semi-automated programming mode, and the second programming mode is the manual programming mode. In this case, the first electrode configuration and the second electrode configuration may be identical. In yet another embodiment, the first programming mode is a first semi-automated programming mode, and the second programming mode is a second semi-automated programming mode. In this case, if the second semi-automated programming mode has a limited number of electrode configurations, defining the second electrode configuration may comprise selecting one of the limited number of electrode configurations that best matches the first electrode configuration, thereby defining the second electrode configuration. The processing circuitry may further be configured for, prior to defining the second electrode configuration, gradually adjusting at least one stimulation parameter (e.g., an electrical stimulation field focus) from a first value corresponding to the first electrode configuration to a second value corresponding to the second electrode configuration.

In an optional embodiment, the system further comprises telemetry circuitry, in which case, the control circuitry may be configured for transmitting the stimulation parameter set(s) to the neurostimulation device via the telemetry circuitry. The system may further comprise a housing containing the user interface, the processing circuitry, and the control circuitry.

In accordance with a second aspect of the present inventions, a method of programming a neurostimulation device coupled to a plurality of electrodes implanted adjacent tissue (e.g., spinal cord tissue) of a patient is provided. The neurostimulation device may be implanted within the patient. The method comprises defining a first electrode configuration corresponding to a first mode of programming the neurostimulation device, selecting a second programming mode different from the first programming mode, defining a second electrode configuration based on the first electrode configuration in response to the selection of the second programming mode, and programming the medical device using the second programming mode. The first and second programming modes, and the manner in which the second electrode configuration is defined can be the same as discussed above. An optional method comprises applying electrical stimulation energy between the first electrode configuration and the tissue, and applying electrical stimulation energy between the second electrode configuration and the tissue.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 15 is a flow diagram illustrating steps for placing the user interface from the e-troll mode or Navigation mode into the manual mode;

FIG. 16 is a flow diagram illustrating steps for placing the user interface from the manual mode into the e-troll mode or Navigation mode;

FIG. 17 is a flow diagram illustrating sub-steps for defining an electrode configuration corresponding to the e-troll or Navigation programming modes based on the last electrode configuration used in the manual programming mode;

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
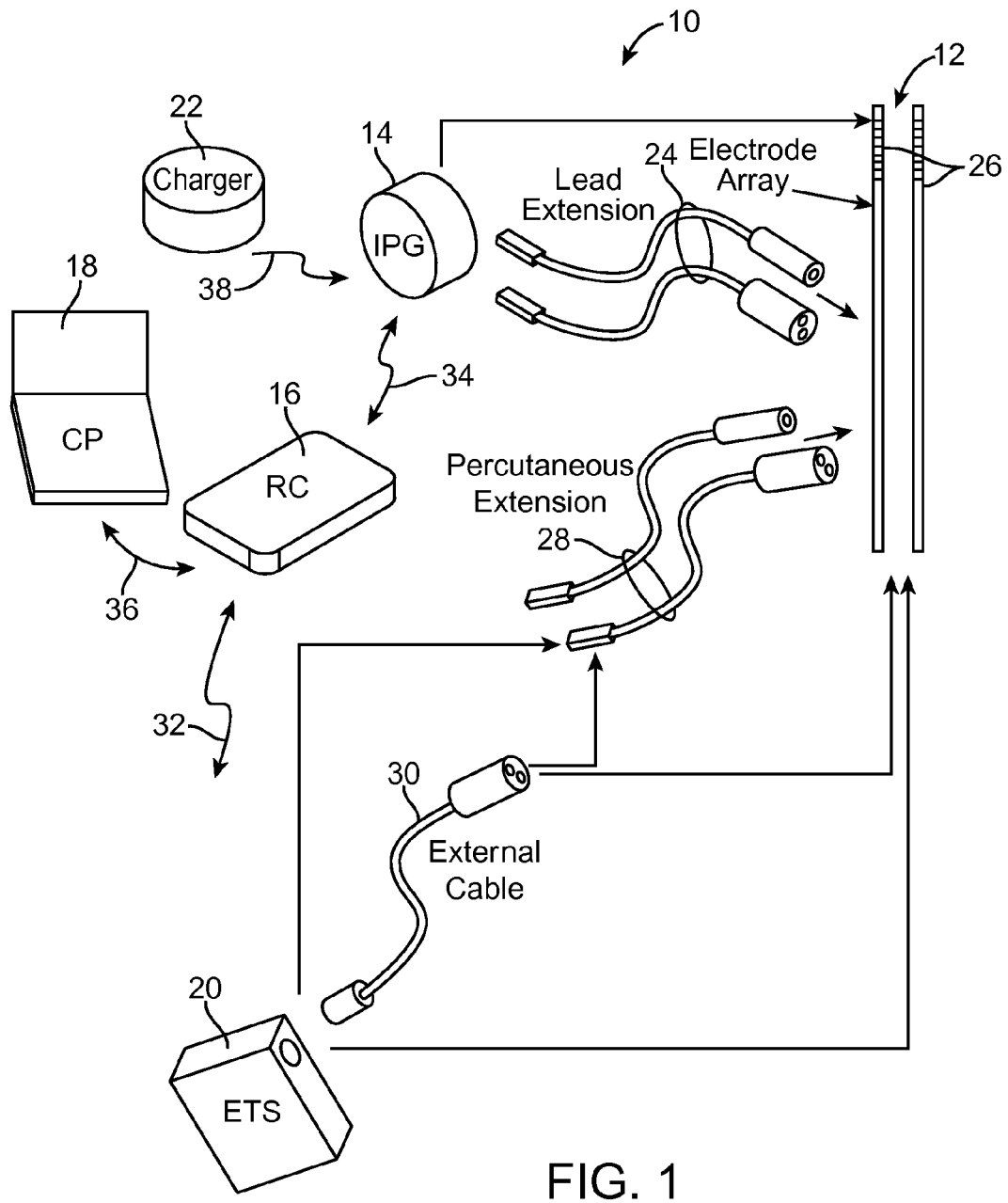
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead in can be used in place of one or more of the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
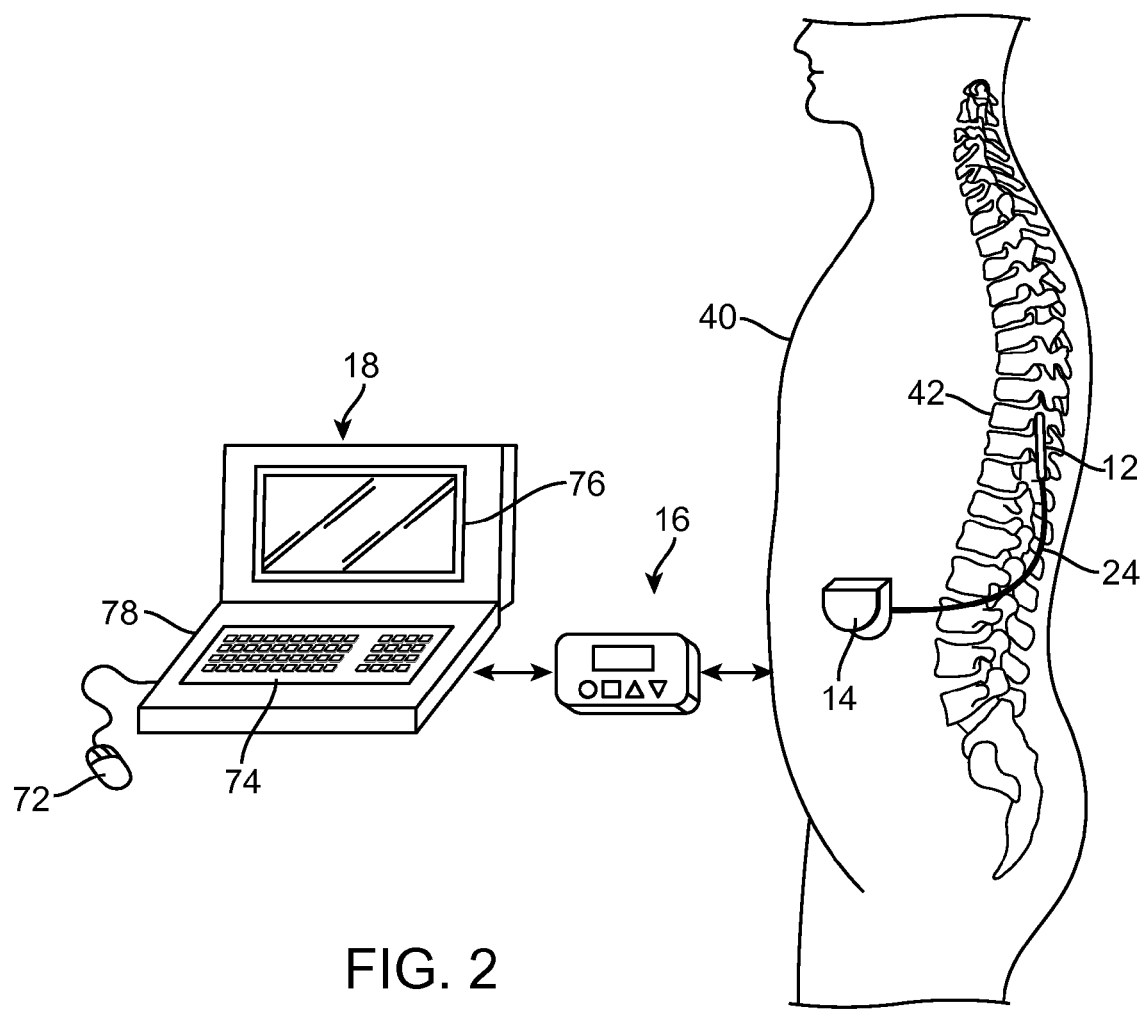
FIG. 2 is a perspective view of the arrangement of the SCS system of FIG. 1 with respect to a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
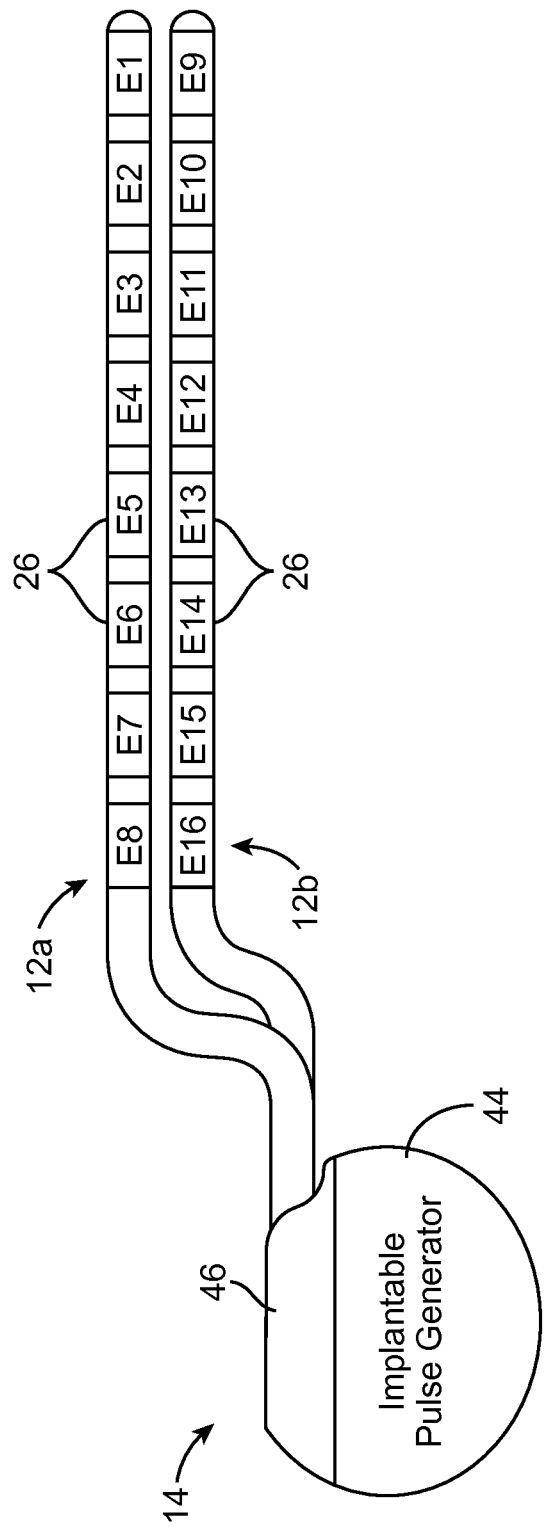
FIG. 3 is a profile view of an implantable pulse generator (IPG) and percutaneous leads used in the SCS system of FIG. 1.

Referring now to FIG. 3, the external features of the neurostimulation leads 12 and the IPG 14 will be briefly described. One of the neurostimulation leads 12a has eight electrodes 26 (labeled E1-E8), and the other stimulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neurostimulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode configurations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
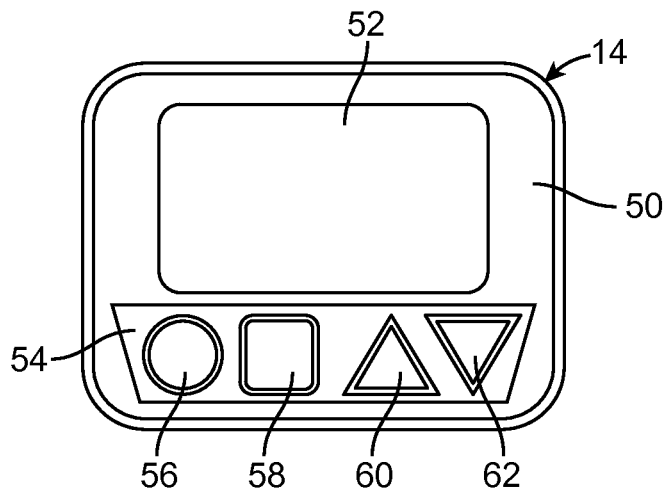
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
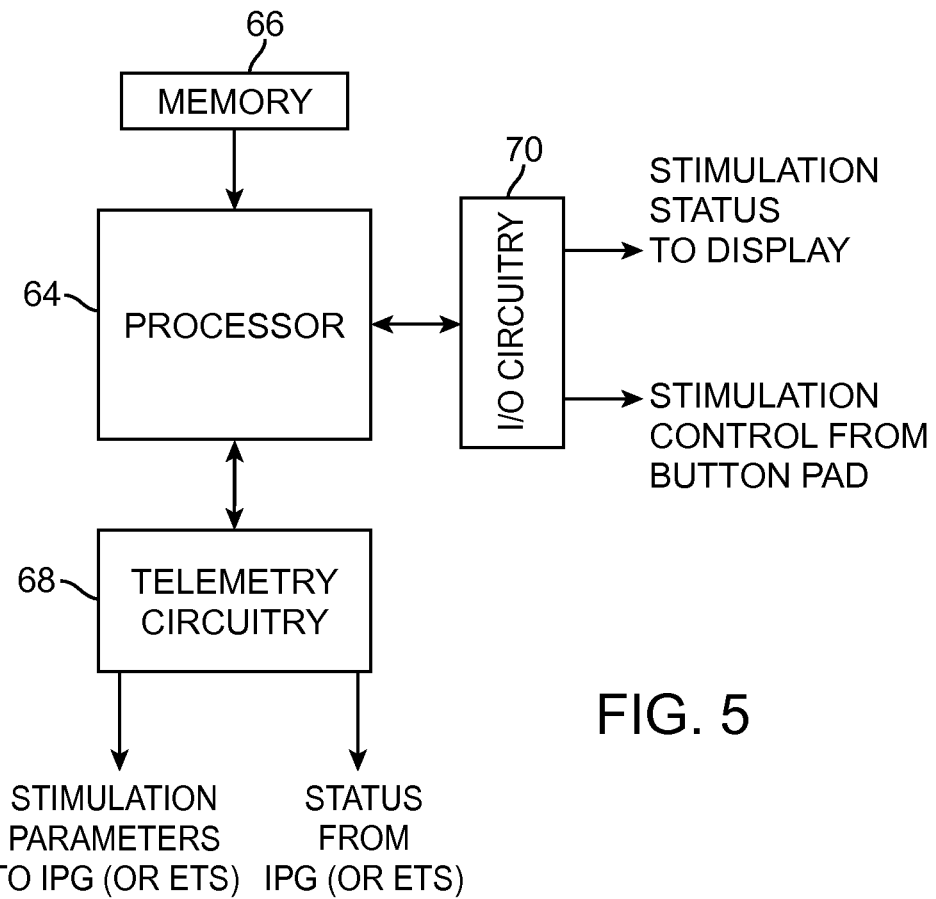
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets, input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode configurations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc, can be used to manipulate graphical objects on the display screen 76. In alternative embodiments, the display screen 76 takes the form of a digitizer touch screen, which may either passive or active. If passive, the display screen 76 includes detection circuitry that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 6:
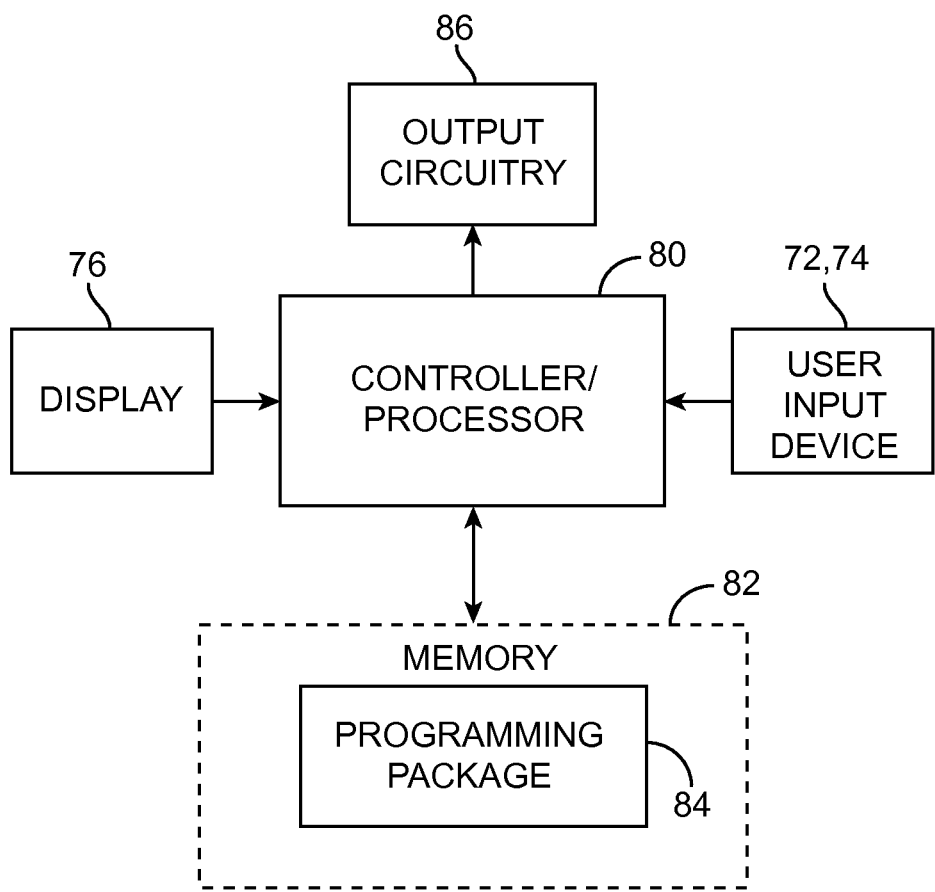
FIG. 6 is a block diagram of the internal components of a clinician's programmer (CP) used in the SCS system of FIG. 1.

As shown in FIG. 6, the CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that conveniently allows a user to program the IPG 14 using different programming modes, and in the illustrated embodiment, three programming modes: a manual programming mode, an e-troll programming mode, and a Navigation programming mode.

Figure 7:
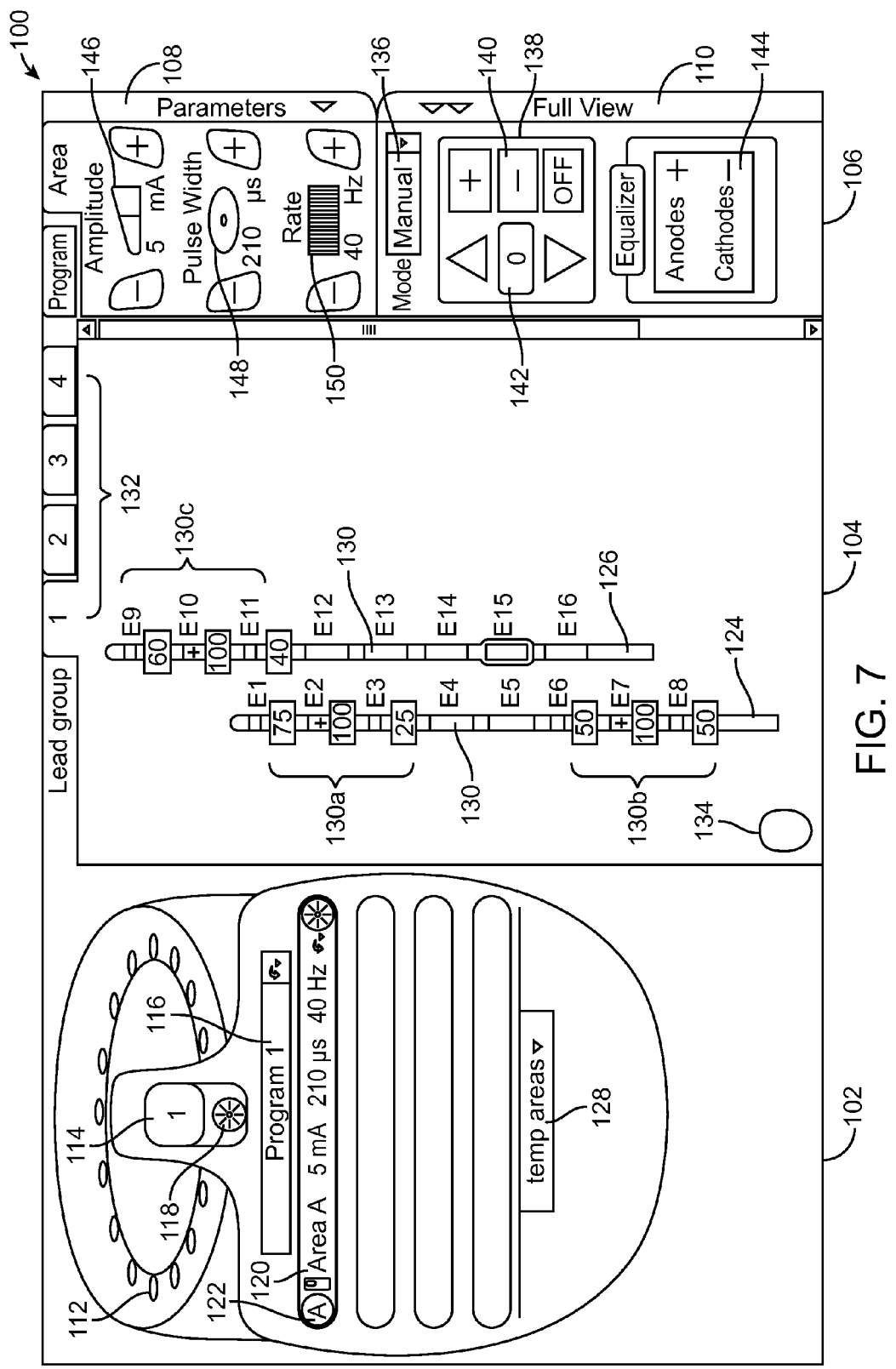
FIG. 7 is a plan view of a user interface of the CP of FIG. 6 for programming the IPG of FIG. 3 in a manual mode.

Referring now to FIG. 7, a graphical user interface (GUI) 100 that can be generated by the CP 18 to allow a user to program the IPG 14 will be described. In the illustrated embodiment, the GUI 100 comprises three panel: a program selection panel 102, a lead display panel 104, and an electrical parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about programs and areas that have been, or may be, defined for the IPG 14. A plurality of programs may be displayed in carousel 112. In the illustrated embodiment, sixteen programs may be defined, but program 1 is the only one currently defined, as shown by the "1" in field 114. Other embodiments may use a carousel or other techniques for displaying available programs with different numbers or arrangements of available program slots.

Each program may be named, as indicated by the name field 116. A stimulation on/off button 118 allows turning the currently active program on or off. When the active program is on, stimulation parameter sets will be generated in the CP 18 and transmitted to the RC 16. Up to four program areas 120 may be defined, allowing a program to control stimulation of multiple areas. Each program area 120 may separately control stimulation of electrodes in the patient, and may be separately turned on or off. Each of the program areas 120 may be labeled with a label 122 that may be used as a marker on the graphical leads 124 and 126, as described below. A number of temporary areas 128 may be used for temporary storage of area information by copying a program area 120 into a temporary area 128 or copying a temporary area 128 into a program area 120. This allows copying a program area 120 from one of the four slots to another slot via one of the temporary areas 128. Other embodiments may also allow copying one of the program areas 120 into another one of the program areas 120 directly. Individual programs may be copied to other slots in the carousel 112 or deleted as desired.

Turning now to the lead display panel 104, graphical leads 124 and 126 are illustrated with eight graphical electrodes 130 each (labeled electrodes E1-E8 for lead 124 and electrodes E9-E16 for lead 126). Other numbers of leads and electrodes per lead may be displayed as desired. In an implanted system using other numbers of electrodes, that number of electrodes may be shown in lead display panel 104. Up to four groups of leads may be viewed by selecting one of the lead group tabs 132. In addition, an icon 134 representing the case 44 of the IPG 14 is displayed in the lead display panel 104. In addition to allocating current to any of the electrodes of graphical leads 124 and 126, current may be allocated to the case 44 as an electrode.

Each of the electrodes 130 of the leads 124 and 126 may be individually selected, allowing the clinician to set the polarity and the magnitude of the current allocated to that electrode 130. In the illustrated embodiment, electrode E15 is currently selected. Electrical current has been allocated to three groups of electrodes respectively corresponding to three programming areas. Electrode group 130a illustrates a single cathode at electrode E2 to which is allocated 100% of the cathodic current and two anodes at electrodes E1 and E3 to which are allocated 25% and 75% of the anodic current, respectively. Electrode group 130b illustrates a single anode at electrode E7 to which is allocated 100% of the cathodic current and two anodes at electrodes E6 and E8 to which are allocated 50% and 50% of the anodic current, respectively. Electrode group 130c illustrates a single anode at electrode E10 to which is allocated 100% of the cathodic current and two anodes at electrodes E9 and E11 to which are allocated 60% and 40% of the anodic current, respectively.

The parameters adjustment panel 106 includes a pull-down programming mode field 136 that allows the user to switch between the manual programming mode, the e-troll programming mode, and the Navigation programming mode. As shown in FIG. 7, the manual programming mode has been selected. In the manual programming mode, each of the electrodes 130 of the graphical leads 124 and 126, as well as the graphical case 132, may be individually selected, allowing the clinician to set the polarity (cathode or anode) and the magnitude of the current (percentage) allocated to that electrode 134 using graphical controls located in the amplitude/polarity area 138. In particular, a graphical polarity control 140 located in the area 138 includes a "+" icon, a "−" icon, and an "OFF" icon, which can be respectively actuated to toggle the selected electrode 134 between a positive polarization (anode), a negative polarization (cathode), and an off-state. An amplitude control 142 in the area 138 includes an arrow that can be actuated to decrease the magnitude of the fractionalized current of the selected electrode 134, and an arrow that can be actuated to increase the magnitude of the fractionalized current of the selected electrode 134. The amplitude control 142 also includes a display area that indicates the adjusted magnitude of the fractionalized current for the selected electrode 134. Amplitude control 142 is preferably disabled if no electrode is visible and selected in the lead display panel 104.

Figure 8:
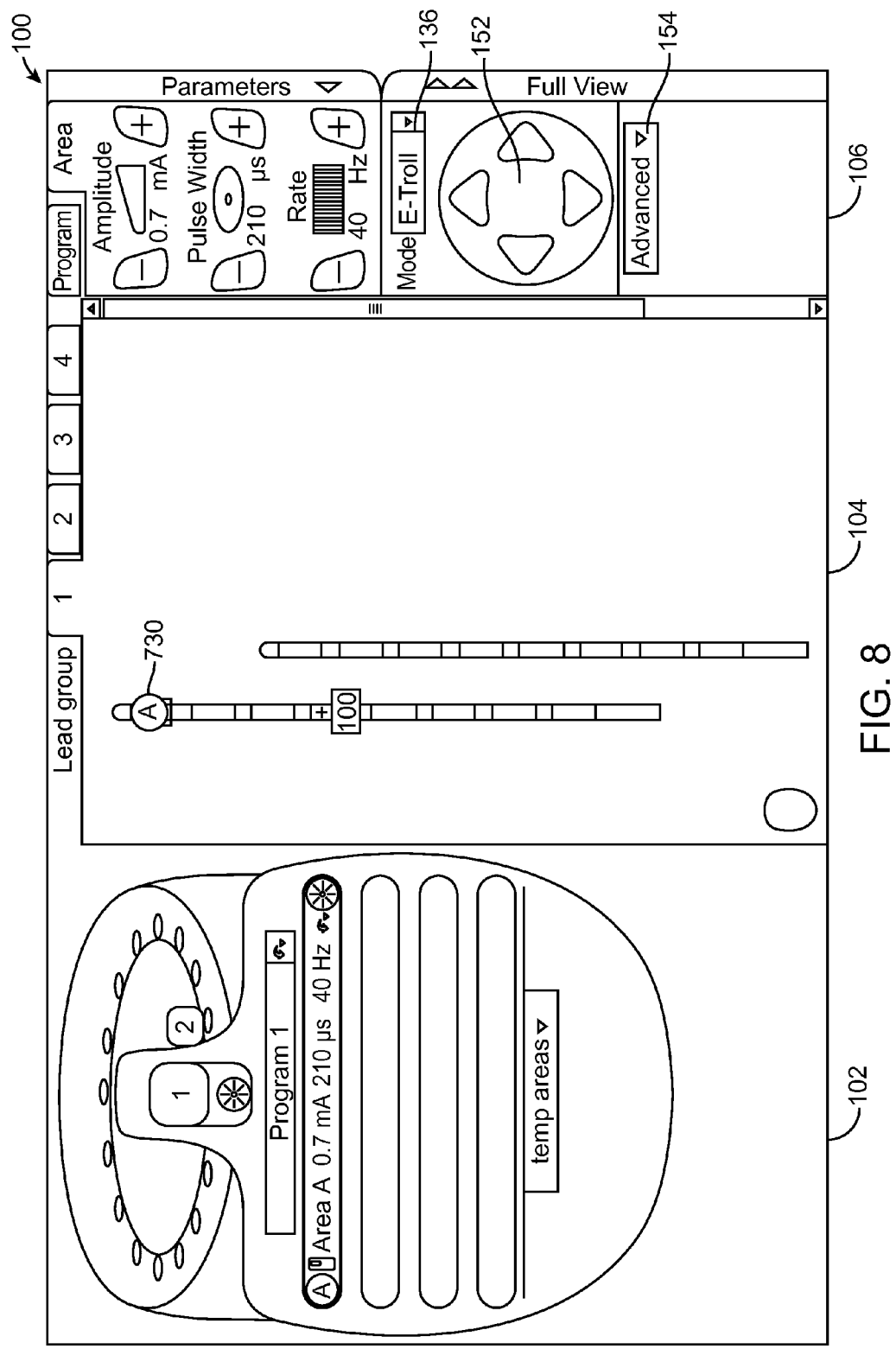
FIG. 8 is a plan view of a user interface of the CP of FIG. 6 for programming the IPG of FIG. 3 in an e-troll mode.
Figure 9:
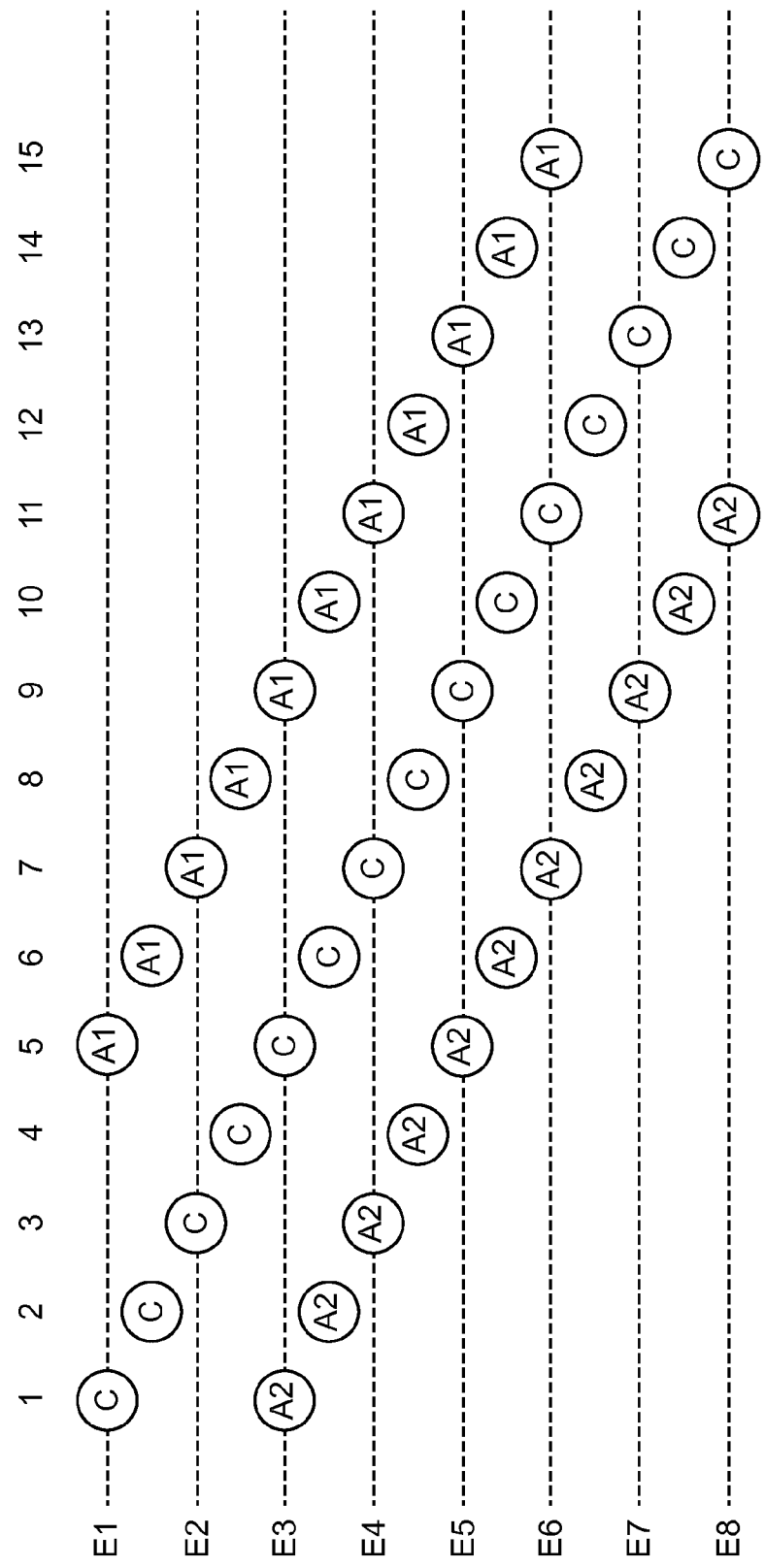
FIG. 9 is a panned sequence of a multipole used by the e-troll mode of FIG. 8 to program the IPG of FIG. 3.

The parameters adjustment panel 106, when the manual programming mode is selected, also includes an equalization control 144 that can be actuated to automatically equalize current allocation to all electrodes of a polarity selected by respective "Anode +" and "Cathode −" icons. The parameters adjustment panel 106 also includes a pulse amplitude adjustment control 150 (expressed in milliamperes (mA)), a pulse width adjustment control 148 (expressed in microseconds (μs)), and a pulse rate adjustment control 146 (expressed in Hertz (Hz)), which are displayed in all three of the programming modes. Each of the controls 146, 148, 150 includes a first arrow that can be actuated to decrease the value of the respective stimulation parameter and a second arrow that can be actuated to increase the value of the respective stimulation parameter. Each of the controls 146, 148, 150 also includes a display area for displaying the currently selected parameter. In the illustrated embodiment, a pulse amplitude of 5 mA, a pulse width of 210 μs, a pulse rate of 60 Hz have been selected. The controls 146, 148, 150 are also displayed in As shown in FIG. 8, the e-troll programming mode has been selected. In this mode, the electrodes 130 illustrated in the lead display panel 104 that were individually selectable and configurable in manual programming mode are used for display only and are not directly selectable or controllable. The parameter selection panel 106 includes a steering array of arrows 152 that allows steering the electrical current up, down, left, or right. In the illustrated embodiment, the electrical current is steered by panning a virtual multipole (i.e., the virtual multipole is moved relative to the actual electrodes 26 without changing the basic configuration (focus (F) and upper anode percentage (UAP)) of the virtual multipole), and computing the electrical amplitude values needed for the actual electrodes 26 to emulate the virtual multipole. For example, as shown in FIG. 9, a series of virtual multipoles, and in this case, tripoles and bipoles, are sequentially defined in accordance with a panned current steering technique over a plurality of dashed lines representing available electrode positions in the electrode array 26.

In the illustrated embodiment, all of the virtual tripoles are symmetrical in that the virtual anodes are equally spaced from the central virtual cathode. The nominal virtual multipoles can also be considered wide tripole/bipoles in that the virtual anode(s) are spaced a relatively large distance from the cathode (in this case, by two electrodes). Between the ends of the electrode array 26, a virtual tripole is panned along the electrode array 26 (i.e., the LGF value is maintained as the virtual cathode is shifted along the electrode array 26). However, as either of the outer virtual anodes of the virtual tripole abuts the last electrode in the array, a virtual bipole is utilized (upper virtual bipole at the top of the electrode array 26, and a lower virtual bipole at the bottom of the electrode array 26). The virtual bipole may then be panned along the electrode array 26 (i.e., the LGF value is maintained as the virtual cathode is shifted along the electrode array 26).

Figure 10:
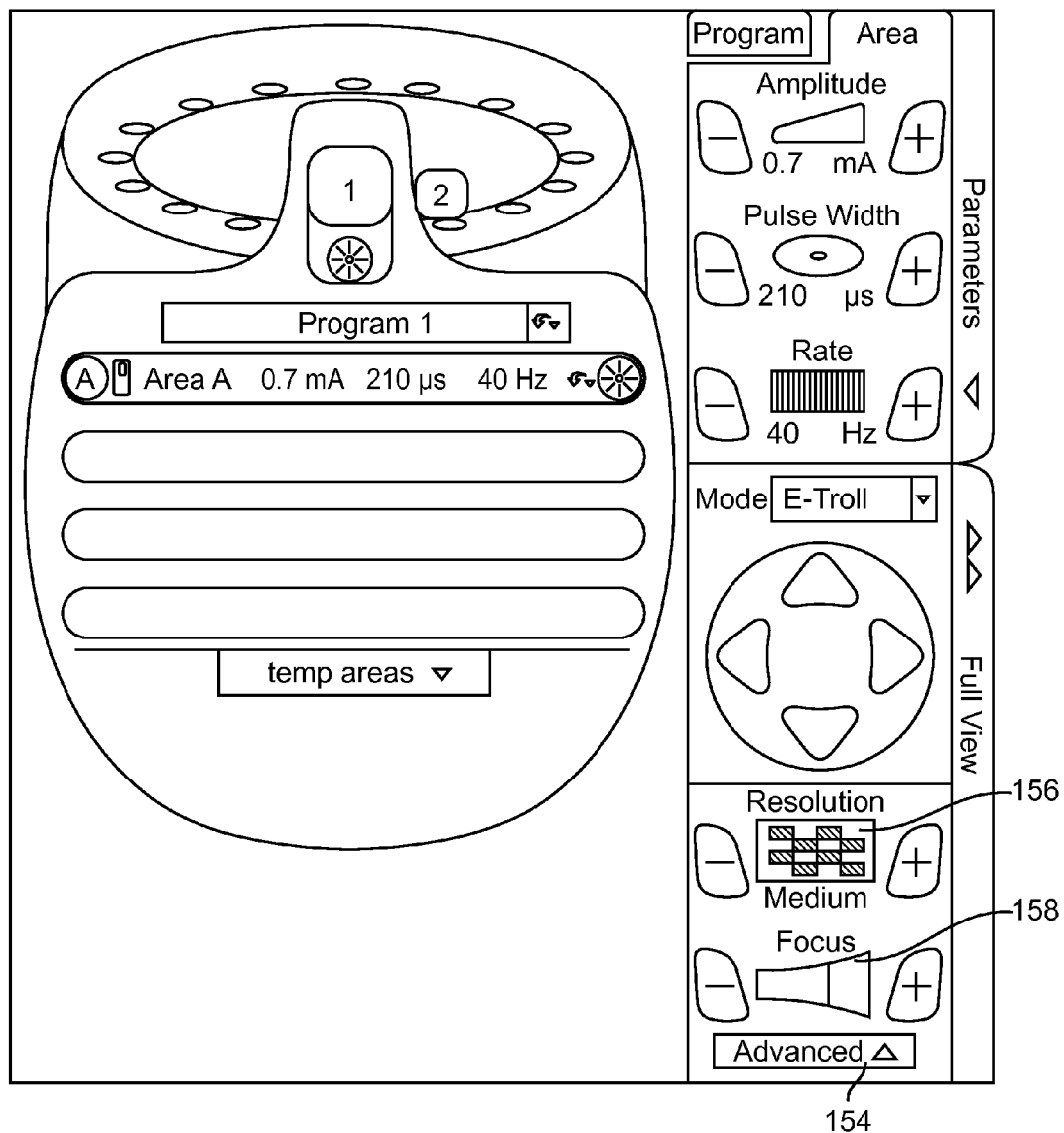
FIG. 10 is a plan view of the user interface of FIG. 8, particularly showing the expansion of the Advanced Tab into resolution and focus controls.

In the e-troll programming mode, the parameter adjustment panel 106 also includes an advanced tab 154, which when actuated, hides the lead display panel 104 and provides access to a resolution control 156 and a focus control 158, as shown in FIG. 10.

The resolution control 156 allows changing the stimulation adjustment resolution. In one embodiment, three possible settings of Fine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering array 152 makes less of a change to the electrode configuration than when the resolution is set to Medium or Coarse. For example, panning of the virtual multipole with a Coarse resolution may displace the virtual multipole relative to the electrode array 26 in steps equivalent to 10% of the electrode spacing, whereas panning of the virtual multipole with a Fine resolution may move the virtual multipole relative to the electrode array 26 in steps equivalent to 1% of the electrode spacing.

The focus control 158 allows changing the stimulation focus by displacing the anode(s) and cathode of the virtual multipole toward each other to increase the focus, or displacing the anode(s) and cathode of the virtual multipole away from each other to decrease the focus. The focus control 158 has a "+" icon and a "−" icon that can be used to adjust the focus. The focus control 158 also includes a display element that graphically displays the current focus level.

Figure 11:
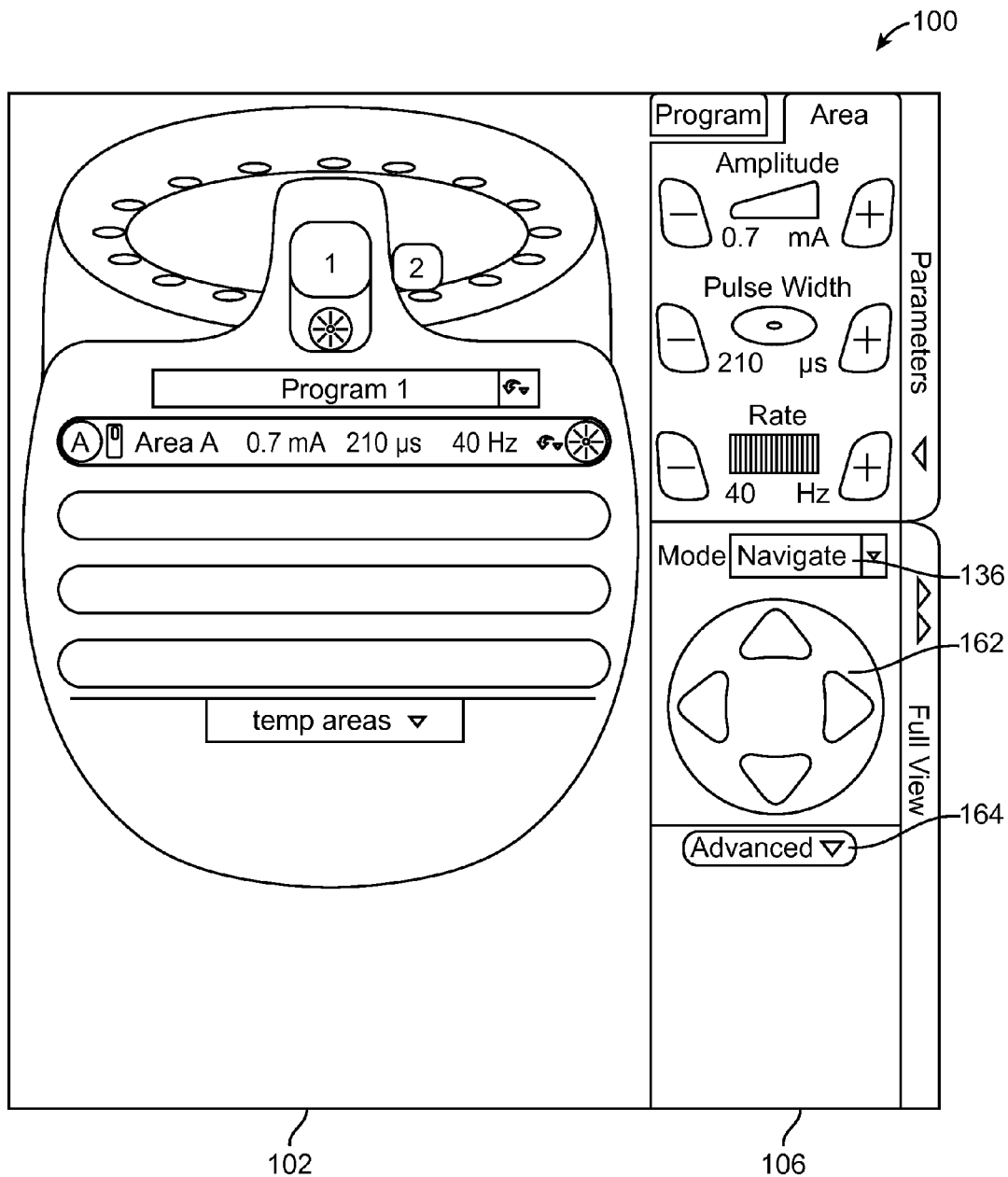
FIG. 11 is a plan view of a user interface of the CP of FIG. 6 for programming the IPG of FIG. 3 in a Navigation mode.

As shown in FIG. 11, the Navigation programming mode has been selected. As in the e-troll programming mode, in the Navigation programming mode, the electrodes illustrated in the lead display panel 104 that were individually selectable and configurable in manual programming mode are used for display only and are not directly selectable or controllable. The parameter selection panel 106 includes a steering array of arrows 162 that allows steering the electrical current up, down, left, or right. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole.

Figure 12:
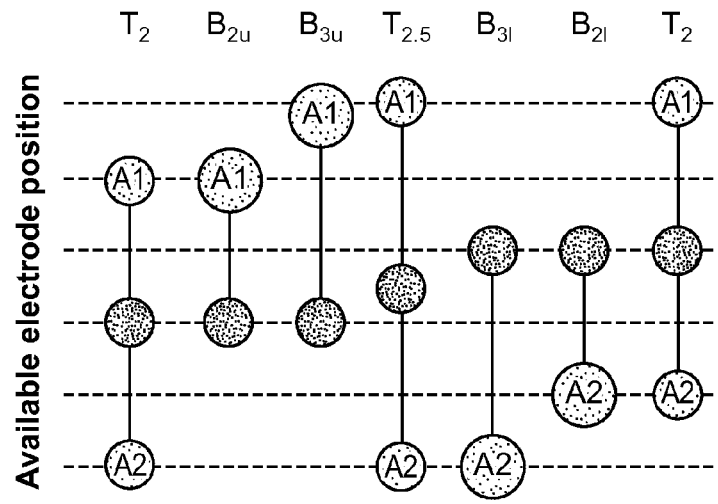
FIG. 12 is a sequence of different virtual multipoles used by the Navigation mode of FIG. 10 to program the IPG of FIG. 3.

For example, as shown in FIG. 12, a series of virtual mutipoles are sequentially defined in accordance with a weaved current steering technique over a plurality of dashed lines representing available electrode positions in the electrode array 26. Each illustrated multipole has a designator indicating whether it is a tripole or bipole (T for tripole and B for bipole), a subscripted designator indicating the longitudinal focus (LGF) in terms of electrode separation, and, in the case of a bipole, a subscripted designator indicating the bipole is an upper bipole (u), meaning that the anode is above the cathode, or the bipole is a lower bipole (l), meaning that the anode is below the cathode.

In the embodiment illustrated in FIG. 12, the different virtual multipoles are sequentially defined in the following order: a narrow virtual tripole ($T_2$), a narrow upper virtual bipole ($B_{2u}$), a wide upper virtual bipole ($B_{3u}$), a wide virtual tripole ($T_{2.5}$), a wide lower virtual bipole ($B_{3l}$), a narrow lower virtual bipole ($B_{2l}$), and the narrow virtual tripole ($T_2$). For purposes of this specification, the terms "narrow" and "wide," when used together to define a virtual bipole or a virtual tripole in either the e-troll programming mode or the Navigation programming mode, are relative terms, and simply mean that the narrow bipole and/or narrow tripole have longitudinal focuses (LGFs) that are less than the longitudinal focuses (LGFs) of the wide bipole and/or wide tripole.

Figure 13:
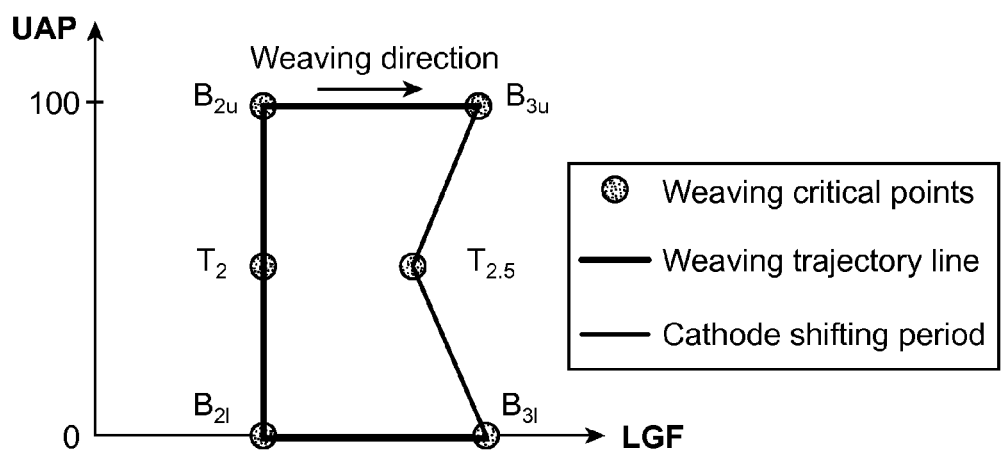
FIG. 13 is a plot illustrating a weaving space for the sequence of the multipoles illustrated in FIG. 12.

The virtual multipoles illustrated in FIG. 12 may be considered critical points between which the cathode position and longitudinal focus (LGF) are incrementally changed by mapping the sequences in a "weave space," defined by the longitudinal focus (LGF) and the upper anode percentage (UAP). As best shown in FIG. 13, the sequence of virtual multipoles is defined by a trajectory line sequentially connecting the critical points (representing by circles) that provides a continuous change in the virtual multipoles.

As can be seen from FIG. 13, the sequence beginning with the narrow virtual tripole ($T_2$) and ending with the narrow upper virtual bipole ($B_{2u}$) incrementally increases the upper anode percentage (UAP) while maintaining the longitudinal focus (LGF). The sequence beginning with the narrow upper virtual bipole ($B_{2u}$) and ending with the wide upper virtual bipole ($B_{3u}$) maintains the upper anode percentage (UAP) while incrementally increasing the longitudinal focus (LGF). The sequence beginning with the wide upper virtual bipole ($B_{3u}$) and ending with the wide virtual tripole ($T_{2.5}$) incrementally decreases the upper anode percentage (UAP) while incrementally decreasing the longitudinal focus (LGF). The sequence beginning with the wide virtual tripole ($T_{2.5}$) and ending with the wide lower virtual bipole ($B_{3l}$) incrementally decreases the upper anode percentage (UAP) while incrementally increasing the longitudinal focus (LGF). The sequence beginning with the wide lower virtual bipole ($B_{3l}$) and ending with the narrow lower virtual bipole ($B_{2l}$) maintains the upper anode percentage (UAP) while incrementally decreasing the longitudinal focus (LGF). The sequence beginning with the narrow lower virtual bipole ($B_{2l}$) and ending with the narrow virtual tripole ($T_2$) incrementally increases the upper anode percentage (UAP) while maintaining the longitudinal focus (LGF).

Notably, the above-mentioned sequence maintains the same position of the virtual cathode relative to the electrode array 26 while transitioning through different types of virtual bipole/tripoles between the narrow virtual tripole ($T_2$) and the wide upper virtual bipole ($B_{3u}$), incrementally changes the position of the virtual cathode relative to the electrode array 26 in one direction (in this case, upward) between the wide upper virtual bipole ($B_{3u}$) and the wide lower virtual bipole ($B_{3l}$), and the maintains the same position of the virtual cathode relative to the electrode array 26 while transitioning through different types of virtual bipole/tripoles between the wide lower virtual bipole ($B_{3l}$) and the narrow virtual tripole ($T_2$). The sequence illustrated in FIG. 12 can be repeatedly cycled through, with the effect being that the virtual cathode is shifted upward by one electrode per each cycle. Further details discussing various weaved current steering techniques are described in U.S. Provisional Patent Application Ser. No. 61/452,965, entitled "Neurostimulation System for Defining a Generalized Virtual Multipole," which has previously been incorporated herein by reference.

In the Navigation programming mode, the parameter adjustment panel 106 also includes the previously described advanced tab 154, which when actuated, hides the lead display panel 104 provides access to the resolution control 156 and the focus control 158 in the same manner described above with respect to the e-troll programming mode in FIG. 10.

The resolution control 156 allows changing the stimulation adjustment resolution. In one embodiment, three possible settings of Fine, Medium, and Coarse may be chosen. When the resolution is set to Fine, each change caused by use of the steering array 162 makes less of a change to the electrode configuration than when the resolution is set to Medium or Coarse. In particular, depending on the resolution, different step sizes may be used transition between the virtual multipoles illustrated in FIG. 12. For example, if the resolution is set to be Fine, a fine resolution (10 steps per critical point transition) may be used to transition between the critical points where the cathode is not being shifted, and an even finer resolution (20 steps per critical point transition) may be used to transition between the critical points where the cathode is being shifted. If the resolution is set to be Coarse, a coarse resolution (5 steps per critical point transition) may be used to transition between all of the critical points.

The focus control 158 allows changing the stimulation focus by displacing the anode(s) and cathode of each of the virtual multipoles toward each other to increase the focus, or displacing the anode(s) and cathode of each of the virtual multipoles away from each other to decrease the focus.

Significantly, when switching between programming modes via actuation of the programming mode field 136, the last electrode configuration with which the IPG 14 was programmed in the previous programming mode is converted into another electrode configuration, which is used as the first electrode configuration with which the IPG 14 is programmed in the subsequent programming mode.

Figure 14:
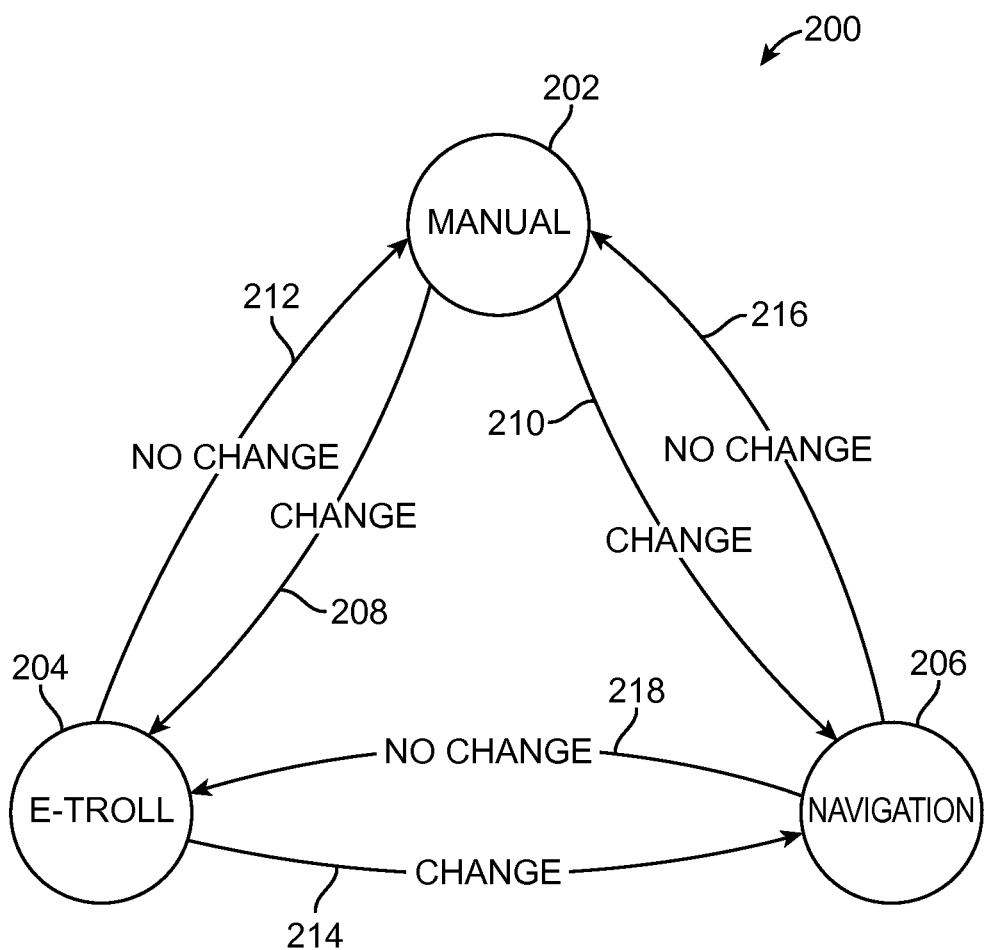
FIG. 14 is a state diagram illustrating transitioning between manual, e-troll, and navigation modes in the user interface of the CP of FIG. 6.

Referring to FIG. 14, a state diagram 200 illustrating one method used by the CP 18 to seamlessly transition between manual, e-troll, and Navigation programming modes will now be described. When in the manual programming mode 202, the CP 18 may transition to the e-troll programming mode 204 using transition 208 or to the Navigation programming mode 206 using transition 210. When in the e-troll programming mode 204, the CP 18 may transition to the manual programming mode using transition 212 or to the Navigation programming mode using transition 214. When in the Navigation programming mode 206, the CP 18 may transition to the manual programming mode using transition 216 or to the e-troll programming mode using transition 218. Transitions 212 and 216 to the manual programming mode may be accomplished without any change to the electrode configuration (i.e., the last electrode configuration used in the e-troll or Navigation programming mode will be identical to the first electrode configuration used in the manual programming mode).

Figure 19:
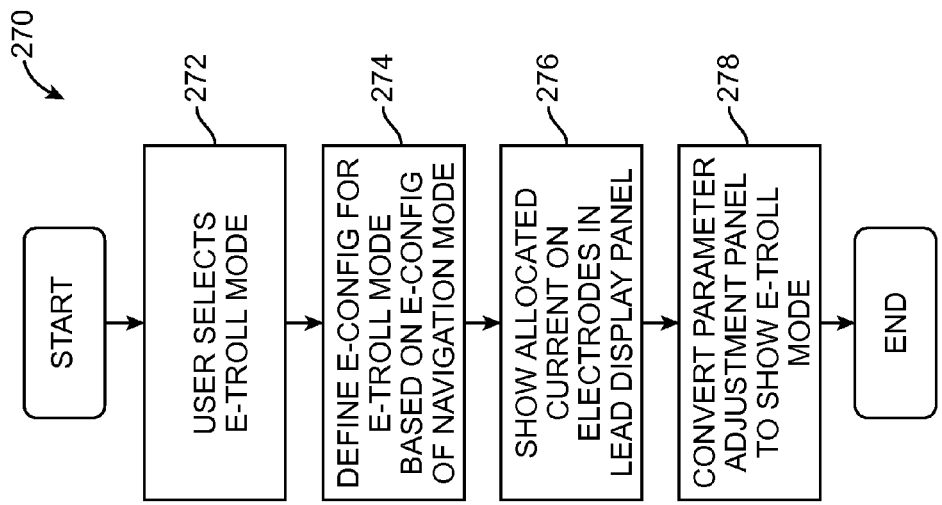
FIG. 19 is a flow diagram illustrating steps for placing the user interface from the Navigation mode into the e-troll mode.

As will be discussed in further detail below, transitions 208, 210, and 214 may require changes to the electrode configurations, depending on the constraints applicable to the e-troll Programming mode 204 or the Navigation programming mode 206. The changes to the electrode configurations may occur at anytime at the beginning of the transitions or at the end of the transitions, but preferably occurs after the user selects a different programming mode. FIG. 15 below illustrates a technique for transitioning from the e-troll programming mode or Navigation programming mode to the manual programming mode; FIG. 16 below illustrates a technique for transitioning from the manual programming mode to the e-troll programming mode or Navigation programming mode; FIG. 19 below illustrates a technique for transitioning from the Navigation programming mode to the e-troll programming mode; and FIG. 20 below illustrates a technique for transitioning from the e-troll programming mode to the Navigation programming mode.

Referring to FIG. 15, one technique 220 for switching from the e-troll programming mode or the Navigation programming mode to the manual programming mode will now be described. The user first selects the manual programming mode by changing the value in the programming mode field 136 of the parameter adjustment panel 106 (step 222). Next, an electrode configuration corresponding to the manual programming mode is defined based on the last electrode configuration used in the e-troll or Navigation programming modes (step 224). Notably, because the manual programming mode allows every possible configuration that may be created in either e-troll or Navigation programming mode, no change to the electrode configuration is made when transitioning from e-troll or Navigation programming mode to manual programming mode, and thus, the electrode configuration corresponding to the e-troll or Navigation programming modes will be identical to the last electrode configuration used in the manual programming mode.

If the lead display panel 104 is visible, the electrodes 134 to which current has been allocated in the last electrode configuration used in the e-troll programming mode or Navigation programming mode are indicated (step 226). The parameter adjustment panel 106 is then changed to its manual programming mode showing the amplitude/polarity area 138 with the graphical polarity control 140 and graphical amplitude control 142 (step 228). Once in the manual programming mode, the clinician may make any desired additional changes to specific electrodes using the graphical polarity control 140 and graphical amplitude control 142.

Referring to FIG. 16, one technique 230 for switching from the manual programming mode to the e-troll programming mode or the Navigation programming mode will now be described. The user first selects the e-troll programming mode or the Navigation programming mode by changing the value in the programming mode field 136 of the parameter adjustment panel 106 (step 232). Next, an electrode configuration corresponding to the e-troll or Navigation programming modes is defined based on the last electrode configuration used in the manual programming mode (step 234). Notably, because the e-troll and Navigation programming modes only allow a subset of all possible configurations of anodes and cathodes, a new and different electrode configuration valid for the selected e-troll programming mode or the Navigation programming mode must be computed.

To this end, and with reference to FIG. 17, the CP 18 computes the centroid of the cathodic current on the electrode array 26 by analyzing the physical locations of the cathodic electrodes and the current distributed on the cathodic electrodes (step 240).

Any desired mathematical technique for calculating a centroid of a collection of points, with the current allocation considered the weight of each electrode, can be utilized. Numerous mathematical techniques for calculating a centroid of a group of weighted points are known to the art and may be used for this calculation. For example, the centroid of the cathodic current can be calculated in accordance with the following equation:

$$\hat{x} = \sum_{i=1}^{n} w_i \cdot x_i; \hat{y} = \sum_{i=1}^{n} w_i \cdot y_i,$$

where $\hat{x}$ is the position of the centroid along the x-axis; $\hat{y}$ is the position of the centroid along the y-axis; i is the electrode designation, n is the number of electrodes; $w_i$ is the percentage current of the electrode i; $x_i$ is the position of the electrode i along the x-axis; and $y_i$ is the position of the electrode i along the y-axis.

Once the centroid of the cathodic current is computed, a virtual multipole having a cathode located at the centroid is assumed (step 242). The focus (F) and upper anode percentage (UAP) of the resulting virtual multipole may depend on the location of the cathode (or centroid) relative the further extent of the electrode array 26. For example, if the cathode is too close to the rostral end of the electrode array 26, the UAP may be zero, effectively utilizing an lower virtual bipole, and if the cathode is too close to the caudal end of the electrode array 26, the UAP may be one hundred percent, effectively utilizing an upper virtual bipole. If the cathode is in the middle of the electrode array 26, the UAP may be arbitrarily selected to be, e.g., fifty percent, thereby evenly distributing the current on the two anodes, or may be computed based on a ratio between the magnitude of anodic current above the computed centroid relative to the magnitude of anodic current below computed centroid. The focus may be determined based on any one of various criteria. For example, the focus may be arbitrarily selected to be, e.g., three; may be selected to match the focus of a predetermined virtual multipole used by the e-troll or Navigation programming modes; or may be computed based on a function of the anodes or anodic current utilized in the manual electrode configuration, e.g., the distance between the position of the centroid of the major anodes above or below the cathodic centroid and the position of the cathodic centroid.

Because the virtual multipole configurations used by the e-troll and Navigation programming mode electrode configurations are limited to a subset of possible configurations, the virtual multipole computed from the original manual programming mode configuration may need to be adjusted to the nearest valid electrode configuration of the e-troll or Navigation programming modes. Thus, the predetermined virtual multipole utilized by the e-troll or Navigation programming modes that best matches the virtual multipole computed from the last electrode configuration used in the manual programming mode is then selected (step 244).

Figure 18:
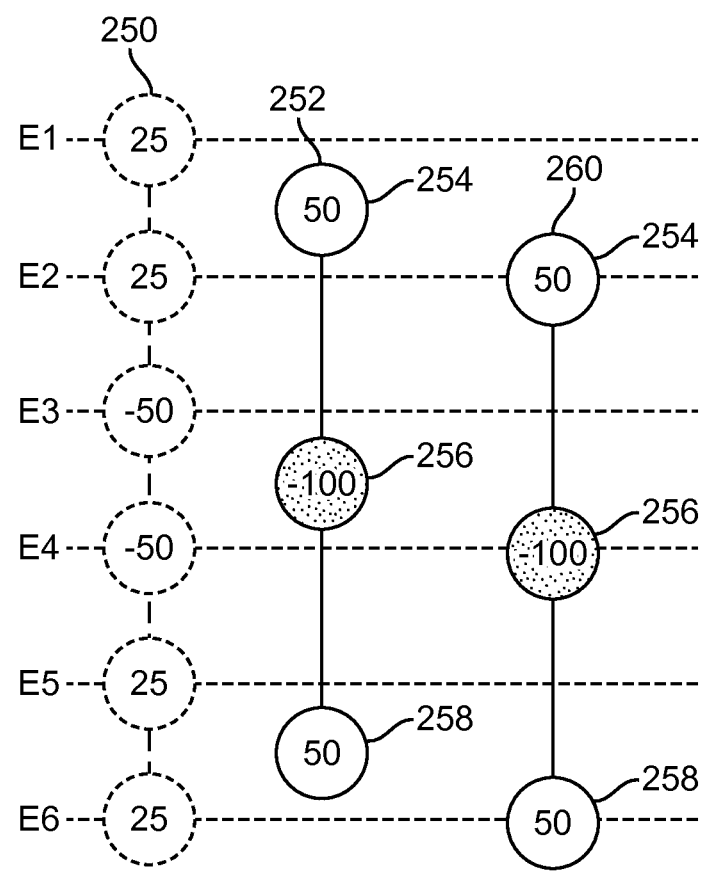
FIG. 18 is a graph illustrating a transition from an exemplary manual mode electrode configuration to an exemplary e-troll electrode configuration.

In one embodiment, the focus of the virtual multipole may be increased or decreased as necessary until the anode or anodes of the virtual tripole create a virtual multipole that is valid for the e-troll or Navigation programming modes. For example, referring to FIG. 18, a graph illustrating a transition from a manual programming configuration to an e-troll configuration will be described. As shown, a virtual tripole 252 is calculated from a manually defined electrode configuration 250 corresponding to steps 240 and 242 of FIG. 17. The virtual tripole 252 has a virtual anode 254, a virtual cathode 256, and a virtual anode 258. In this example, the virtual tripole 252 is not a valid configuration for the e-troll programming mode, which in the illustrated embodiment, is asymmetrical, having a focus of 2 between the virtual anode 254 and the virtual cathode 256, and a focus of 2.5 between the virtual anode 258 and the virtual cathode 256. To convert from manual to e-troll programming mode, as in step 244 of FIG. 17, the asymmetrical virtual tripole 252 is changed to a symmetrical virtual tripole 260 with a focus of 2.

Referring back to FIG. 17, once a virtual multipole valid for the e-troll programming mode or the Navigation programming mode is determined, the electrical amplitude values needed for the electrodes 26 to emulate this virtual multipole configuration are computed (step 246).

Referring back to FIG. 16, if the lead display panel 104 is visible, the electrodes 26 to which current has been allocated in the last electrode configuration used in the e-troll programming mode or Navigation programming mode are indicated (step 236). The parameter adjustment panel 106 is then changed to its e-troll or Navigation programming mode showing the steering array of arrows 154 (for e-troll programming mode) or the steering array of arrows 162 (for Navigation programming mode) (step 238).

Referring to FIG. 19, one technique 270 for switching from the Navigation programming mode to the e-troll programming mode will now be described. The user first selects the e-troll programming mode by changing the value in the programming mode field 136 of the parameter adjustment panel 106 (step 272). Next, an electrode configuration corresponding to the e-troll programming mode is defined based on the last electrode configuration used in the Navigation programming mode (step 274).

Notably, because Navigation and e-troll programming modes support different subsets of all possible electrode configurations, a virtual multipole in the Navigation programming mode may not match one of the predetermined configurations typically utilized by the e-troll programming mode. However, even though the focus (F) and/or upper anode percentage (UAP) of the last virtual multipole used in the Navigation programming mode may not be the same as that of the virtual multipoles typically used by the e-troll programming mode, the virtual multipole of the Navigation programming mode may be used as the starting virtual multipole in the e-troll programming mode. Thus, in this case, the initial virtual multipole used in the e-troll programming mode is identical to the last virtual multipole used in the Navigation programming mode. The same electrical amplitude values needed for the electrodes 26 to emulate the last virtual multipole used in the Navigation programming mode are used to emulate the initial virtual multipole used in the Navigation programming mode.

If the lead display panel 104 is visible, the electrodes 26 to which current has been allocated in the last electrode configuration used in the e-troll programming mode or Navigation programming mode are indicated (step 276). The parameter adjustment panel 106 is then changed to its e-troll programming mode showing the steering array of arrows 154 (step 278). Once in the e-troll programming mode, the clinician may pan the virtual multipole via the steering array of arrows 154 without changing the F and UAP.

Figure 20:
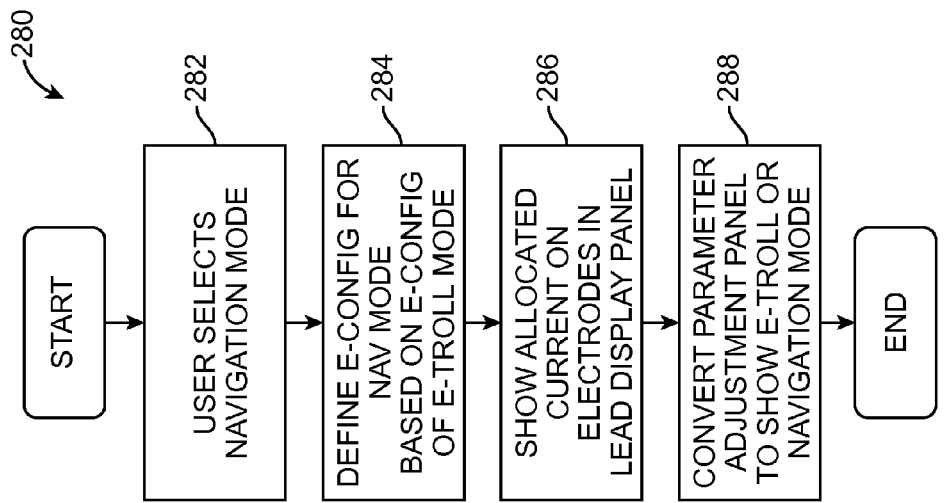
FIG. 20 is a flow diagram illustrating steps for placing the user interface from the e-troll mode into the Navigation mode.

Referring to FIG. 20, one technique 280 for switching from the e-troll programming mode to the Navigation programming mode will now be described. The user first selects the Navigation programming mode by changing the value in the programming mode field 136 of the parameter adjustment panel 106 (step 282). Next, an electrode configuration corresponding to the Navigation programming mode is defined based on the last electrode configuration used in the Navigation programming mode (step 284). Notably, because Navigation and e-troll programming modes support different subsets of all possible electrode configurations, a virtual multipole in the Navigation programming mode may not match one of the predetermined configurations utilized by the e-troll programming mode, and thus, a new and different electrode configuration valid for the selected Navigation programming mode may be need to be computed.

In one embodiment, a smooth transition from the electrode configuration of the e-troll programming mode configuration to the electrode configuration of the Navigation programming mode is accomplished by prompting the user to adjust the focus of the virtual multipole via the focus control 158 illustrated in FIG. 10 until its focus matches one of the predetermined Navigation programming configurations. During this step, the CP 18 may restrict access to parameters other than focus, such as the navigation arrows, and then, after matching a predetermined Navigation programming configuration, may allow access to non-focus parameters.

Figure 21:
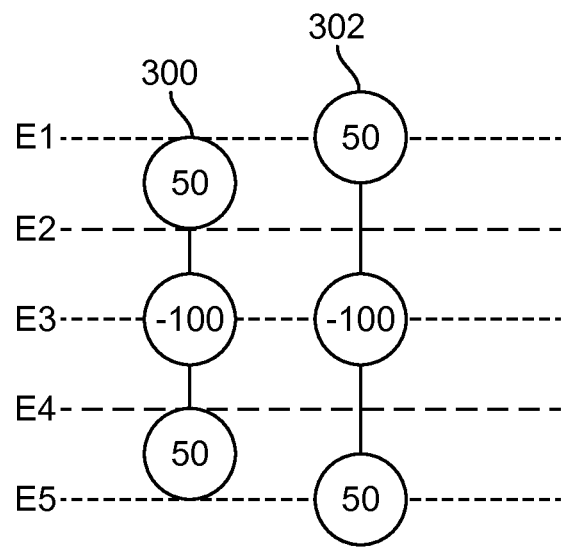
FIG. 21 is a graph illustrating a transition from an exemplary e-troll electrode configuration to an exemplary Navigation electrode configuration.

For example, referring to FIG. 21, a graph illustrating a transition from an e-troll programming configuration to a Navigation programming configuration will be described. As shown, a virtual tripole 300 is illustrated indicating the location of the cathode at electrode E3, a focus of a one and half electrode spacing, and an upper anode percentage of fifty. Because the virtual tripole 300 in this example is not a valid configuration for the Navigation programming mode, when switching from e-troll programming mode to Navigation programming mode a transition may be made by widening the focus from a one and half electrode spacing to a two-electrode spacing to generate a virtual tripole 302.

Once a multipole valid for the Navigation programming mode is determined, the electrical amplitude values needed for the electrodes 26 to emulate this virtual multipole configuration are computed (step 280). The parameter adjustment panel 106 is then changed to its Navigation programming mode showing the steering array of arrows 162 (for Navigation programming mode) (step 282). Once in the Navigation programming mode, the clinician may sequence through the predetermined serious of virtual multipole configurations via the steering array of arrows 154.

It can be appreciated from the foregoing, by providing a GUI and underlying software that allows transitioning between manual, e-troll, and Navigation programming modes without requiring a clinician to restart the configuration process in the destination mode, various embodiments described above provide a less cumbersome and more effective tool for programming implantable medical devices.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating a system that includes a plurality of electrodes and a neurostimulation device coupled to the plurality of electrodes, the method comprising:
    actuating a programming selection control element on a user interface;
    selecting one of different programming modes for the neurostimulation device in response to the actuation of the programming selection control element;
    defining a first electrode configuration corresponding to the first programming mode;
    actuating the programming selection control element on the user interface again;
    selecting the second programming mode in response to the actuation of the programming selection control element again;
    defining a second electrode configuration based on the first electrode configuration in response to the selection of the second programming mode, the second electrode configuration corresponding to the second programming mode;
    generating a stimulation parameter set corresponding to the second electrode configuration; and
    conveying electrical energy from the neurostimulation device to the plurality of electrodes in accordance with the stimulation parameter set.

2. The method of claim 1, wherein the first electrode configuration is not a valid electrode configuration for the second programming mode.

3. The method of claim 1, wherein the second electrode configuration approximates the first electrode configuration.

4. The method of claim 1, wherein each of the first and second electrode configurations is a fractionalized electrode configuration.

5. The method of claim 1, wherein the first programming mode is one of a manual programming mode and a semi-automated programming mode, and the second programming mode is the other of the manual programming mode and the semi-automated programming mode.

6. The method of claim 5, further comprising:
    defining a virtual multipole relative to the plurality of electrodes when programming the neurostimulation device in the semi-automated mode; and
    computing amplitude values for the plurality of electrodes that emulate the virtual multipole, wherein the stimulation parameter set includes the computed amplitude values.

7. The method of claim 6, wherein the semi-automated programming mode pans the virtual multipole across the plurality of electrodes.

8. The method of claim 6, wherein the virtual multipole includes at least one anode and a cathode, and the semi-automated programming mode displaces the at least one anode relative to the cathode as the cathode is gradually displaced across the plurality of electrodes.

9. The method of claim 5, wherein the first programming mode is the manual programming mode, and the second programming mode is the semi-automated programming mode.

10. The system of claim 9, wherein the second electrode configuration is defined by:
    computing a centroid of cathodic current of the first electrode configuration;
    defining a virtual multipole having a virtual cathode located at the centroid of the cathodic current; and
    computing current amplitude values for the plurality of electrodes that emulates the virtual multipole, thereby defining the second electrode configuration.

11. The method of claim 5, wherein the first programming mode is the semi-automated programming mode, and the second programming mode is the manual programming mode.

12. The method of claim 11, wherein the first electrode configuration and the second electrode configuration are identical.

13. The method of claim 1, wherein the first programming mode is a first semi-automated programming mode, and the second programming mode is a second semi-automated programming mode.

14. The method of claim 13, wherein the second semi-automated programming mode has a limited number of electrode configurations, and wherein defining the second electrode configuration comprises selecting one of the limited number of electrode configurations that best matches the first electrode configuration, thereby defining the second electrode configuration.

15. The method of claim 14, further comprising, prior to defining the second electrode configuration, gradually adjusting at least one stimulation parameter from a first value corresponding to the first electrode configuration to a second value corresponding to the second electrode configuration.

16. The method of claim 15, wherein the at least one stimulation parameter comprises an electrical stimulation field focus.

17. A method of operating a system that includes a plurality of electrodes and a neurostimulation device coupled to the plurality of electrodes, the method comprising:
   actuating a programming selection control element on a user interface;
   selecting one of different programming modes for the neurostimulation device in response to the actuation of the programming selection control element;
   defining a first electrode configuration corresponding to the first programming mode;
   actuating the programming selection control element on the user interface again;
   selecting the second programming mode in response to the actuation of the programming selection control element again;
   defining a second electrode configuration based on the first electrode configuration in response to the selection of the second programming mode, the second electrode configuration corresponding to the second programming mode;
   generating a stimulation parameter set corresponding to the second electrode configuration; and
   conveying electrical energy from the neurostimulation device to the plurality of electrodes in accordance with the stimulation parameter set,
   wherein the second electrode configuration approximates the first electrode configuration, and each of the first and second electrode configurations is a fractionalized electrode configuration.

18. The method of claim 17, wherein the first electrode configuration is not a valid electrode configuration for the second programming mode.

19. The method of claim 17, wherein the first programming mode is one of a manual programming mode and a semi-automated programming mode, and the second programming mode is the other of the manual programming mode and the semi-automated programming mode.

20. The method of claim 17, wherein the first programming mode is the manual programming mode, and the second programming mode is the semi-automated programming mode.

* * * * *